(12) United States Patent
Hoogenboom

(10) Patent No.: US 9,180,202 B2
(45) Date of Patent: Nov. 10, 2015

(54) POLYOXAZOLINE POLYMERS AND METHODS FOR THEIR PREPARATION, CONJUGATES OF THESE POLYMERS AND MEDICAL USES THEREOF

(71) Applicant: Universiteit Gent, Ghent (BE)

(72) Inventor: Richard Hoogenboom, Terneuzen (NL)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/370,181

(22) PCT Filed: Dec. 28, 2012

(86) PCT No.: PCT/NL2012/050933
§ 371 (c)(1),
(2) Date: Jul. 1, 2014

(87) PCT Pub. No.: WO2013/103297
PCT Pub. Date: Jul. 11, 2013

(65) Prior Publication Data
US 2015/0025196 A1      Jan. 22, 2015

(30) Foreign Application Priority Data

Jan. 2, 2012   (WO) ................ PCT/NL2012/050001
Mar. 16, 2012   (EP) ..................................... 12159986

(51) Int. Cl.
| A61K 47/48 | (2006.01) |
| A61K 51/06 | (2006.01) |
| C08G 73/02 | (2006.01) |
| C08L 79/02 | (2006.01) |
| A61K 47/34 | (2006.01) |

(52) U.S. Cl.
CPC ........... *A61K 47/48192* (2013.01); *A61K 47/34* (2013.01); *A61K 47/48* (2013.01); *A61K 47/48007* (2013.01); *A61K 47/48169* (2013.01); *A61K 47/48246* (2013.01); *A61K 51/06* (2013.01); *A61K 51/065* (2013.01); *C08G 73/0233* (2013.01); *C08L 79/02* (2013.01)

(58) Field of Classification Search
CPC . A61K 47/34; A61K 47/48; A61K 47/48007; A61K 47/48169; A61K 47/48192; A61K 51/06; A61K 51/065; C08G 73/0233; C08L 79/02

See application file for complete search history.

(56) References Cited

U.S. PATENT DOCUMENTS

| 3,996,237 A | 12/1976 | Tomalia |
| 5,635,571 A | 6/1997 | Frechet et al. |
| 6,566,406 B1 | 5/2003 | Pathak et al. |
| 2002/0042473 A1 | 4/2002 | Trollsas et al. |
| 2003/0119985 A1 | 6/2003 | Sehl et al. |
| 2004/0157157 A1 | 8/2004 | Saito et al. |
| 2005/0002893 A1 | 1/2005 | Goldmann |
| 2011/0123453 A1 | 5/2011 | Bentley et al. |

FOREIGN PATENT DOCUMENTS

| GB | 0 760 311 A | 10/1956 |
| GB | 1 164 582 A | 9/1969 |
| JP | 2005-161698 A | 6/2005 |
| WO | WO-00/71600 A1 | 11/2000 |
| WO | WO-02/062276 | 8/2002 |
| WO | WO-02/102864 A1 | 12/2002 |
| WO | WO-2006/034128 A2 | 3/2006 |
| WO | WO-2006/078282 A2 | 7/2006 |
| WO | WO-2009/043027 A2 | 4/2009 |
| WO | WO-2009/089542 A2 | 7/2009 |
| WO | WO-2009/112402 A1 | 9/2009 |
| WO | WO-2010/033207 A1 | 3/2010 |
| WO | WO-2010/043979 A2 | 4/2010 |

OTHER PUBLICATIONS

Bentolila, A. et al., "Poly(N-acryl amino acids): A new class of biologically active polyanions", Journal of Medicinval Chemistry, American Chemical Society, vol. 43, Jan. 1, 2000, pp. 2591-2600.

(Continued)

*Primary Examiner* — Robert Jones, Jr.
(74) *Attorney, Agent, or Firm* — Gilberto M. Villacorta; Sunit Talapatra; Foley & Lardner LLP

(57) ABSTRACT

The present invention relates to functionalized ploy(2-oxazoline) polymers, which are very suitable as a carrier and/or delivery vehicle (conjugate) of drugs, such as small therapeutic molecules and bio-pharmaceuticals. These polymers are characterized in that they comprise repeating units that are represented by the following formula —[N(R$^1$)—(CHR$^2$)m]- wherein R$^1$ is R$^3$—(CHR$^4$)n-CONH—R$^5$; R$^2$ is selected from H and optionally substituted C$_{1-5}$alkyl; R$^3$ is CH$_2$CO, C(O)O, C(O)NH OR C(S)NH; R$^4$ is selected from H and optionally substituted C$_{1-5}$alkyl; R$^5$ is H; an C$_{1-5}$alkyl; aryl; or a moiety comprising a functional group that can be used for conjugation; m is 2 or 3 and n is 1-5; or n is 0 and R$^3$ is CH$_2$. The invention relates further to a conjugate of these polyoxazoline polymers with at least one active moiety, such as a therapeutic moiety, a targeting moiety and/or diagnostic moiety, and to the use of these conjugates in the therapeutic treatment or prophylactic treatment or diagnosis of a disease or disorder.

20 Claims, No Drawings

(56) References Cited

OTHER PUBLICATIONS

Chujo, et al. "Reversible Gelation of Polyoxazoline by Means of Diels-alder Reaction", Macromolecules, 1990, vol. 23, pp. 2636-2641.

Diehl Christina et al, "Thermo-responsive polyoxazolines with widely tuneable LCSTa", Database Medline, US National Library of Medicine, Feb. 2009, vol. 9, No. 2, pp. 157-161.

Inata, H. et al., "Postcrosslinking of linear polyesters. II. UV-induced crosslinking agents having carboxyl reactive group", Journal of Applied Polymer Science, vol. 36, No. 7, 1988, pp. 1667-1672.

International Search Report in PCT/NL2012/050001 dated May 16, 2012.

International Search Report in PCT/NL2012/050933 dated May 7, 2013.

Luxenhofer, et al. "Novel Functional Poly(2-oxazoline)s as Potential Carriers for Biomedical Applications. Dissertation", Internet Citation, 2007, XP008138013, http://mediatum2.ub.tum.de/doc/620620/document.pdf. (Table of Contents).

Mero, et al. "Synthesis and characterization of poly(2-ethyl2-oxazoline)-conjugates with proteins and drugs: Suitable alternatives to PEG-conjugates?", Journal of Controlled Release, Oct. 2007, vol. 125, No. 2, pp. 87-95.

Richter, R. et al., "Uber die Umsetzungen von 2-alkyl-Delta2-oxazolinen und 2-methyl-Delta2-thiazolin mit Arylisocyanaten", Liebigs Ann. Chem., vol. 743, 1971, pp. 10-24.

Santini, et al. "Synthesis and Bulk Assembly Behavior of Linear-Dendritic Rod Diblock Copolymers", Journal of Polymer Science: Part A: Polymer Chemistry, (2004). vol. 42, pp. 2784-2814.

Cesana, et al. "First Poly(2-oxazoline)s with Pendant Amino Groups", Macromolecular Chemistry and Physics, (2006), vol. 207, pp. 183013192.

Liu, et al. "Shell Cross-Linked Micelle-Based Nanoreactors for the Substrate-Selective Hydrolytic Kinetic Resolution of Epoxides", J. Am. Chem. Soc., (2011), vol. 133, 1426001314263.

Zarka, et al. "Amphiphilic Polymer Supports for the Asymmetric Hydrogenation of Amino Acid Precursors in Water", Chem. Eur. J. (2003), vol. 9, pp. 3228-3234.

POLYOXAZOLINE POLYMERS AND METHODS FOR THEIR PREPARATION, CONJUGATES OF THESE POLYMERS AND MEDICAL USES THEREOF

CROSS-REFERENCE TO RELATED APPLICATIONS

This application is the National Phase of International Patent Application No. PCT/NL2012/050933, filed Dec. 28, 2012, published as WO 2013/103297, which claims priority to International Patent Application No. PCT/NL2012/050001, filed Jan. 2, 2012 and European Application No. 12159986.4, filed Mar. 16, 2012. The contents of these applications are herein incorporated by reference in their entirety.

TECHNICAL FIELD OF THE INVENTION

The invention relates to polyoxazoline polymers containing one or more pendant units with an amide group and to a method for preparing such polymers. The invention relates further to a conjugate of these polyoxazoline polymers with at least one active moiety, such as a therapeutic moiety, a targeting moiety and/or diagnostic moiety, and to the use of these conjugates in the therapeutic treatment or prophylactic treatment or diagnosis of a disease or disorder.

BACKGROUND OF THE INVENTION

The ever increasing human life span poses a continuous demand to the pharmaceutical and biotechnology market for improving the therapeutic efficacy of drugs. However, there are major drawbacks associated with conventional dosage forms, such as fast renal clearance of small drugs and enzymatic degradation of biopharmaceuticals.

Common problems encountered in the use of small molecule drugs, especially for anti-tumor therapeutics, are their low solubility, rapid excretion and untargeted systemic biodistribution leading to severe toxic side effects.

Although more and more biopharmaceuticals are in development, many of these pharmaceuticals have problems that are typical of polypeptide therapeutics, such as short circulating half-life, immungenicicty, proteolytic degradation, and low solubility.

Several strategies have emerged as ways to improve the pharmacokinetic and pharmacodynamic properties of pharmaceuticals. Examples of such strategies are; manipulation of the amino-acid sequence of biopharmaceuticals to decrease immunogenicity and proteolytic cleavage; fusion or conjugation of small molecules or biopharmaceuticals to immunoglobulines and serum proteins, such as for example albumin; incorporation of pharmaceuticals into drug delivery verhicles for protection and slow release; and conjugating to natural or synthetic polymers.

The most commonly used polymer conjugation strategy is the coupling of poly(ethylene glycol) (PEG) to the small molecule pharmaceutical or bio-pharmaceutical. Important precedents of PEGylation already demonstrated improved therapeutic efficacies leading to commercial applications of PEGylated bio-pharmaceuticals, such as enzymes, cytokines and antibodies, as well as a PEGylated liposome carriers for the anticancer drug Doxorubicin.

PEG is an attractive polymer for drug conjugation since it increases the hydrodynamic radius of a drug and shields it, at least partially, from interactions with the body, including the immune system and proteolytic enzymes. Especially this latter shielding property is the main driving force for the success of PEG, compared to many other water soluble polymers, which is believed to result form the good hydration of PEG. By increasing the molecular weight of a molecule through PEGylation, several significant pharmacological advantages over the unmodified form arise, such as an improved drug solubility, extended circulating half-life, reduced immunogenicity, increased drug stability and an improved protection against proteolytic degradation.

Despite the common use of PEGylation there are several disadvantages associated with its use. Sometimes, hypersensitivity and the formation of PEG antibodies is observed. It is also observed that when PEG with high molecular weights is used, it accumulates in the liver, leading to the so called macromolecular syndrome. The chain length of the PEG molecules may be reduced under the influence of enzymes, such as P450 or alcoholdehydrogenase, giving rise to toxic side products.

With respect to small therapeutic molecules it is often observed that with PEG only a relatively low drug loading can be achieved due to the presence of merely one or two hydroxyl terminal groups that can be activated. Furthermore, orthogonal functionalization of PEG or PEG dendrons with the therapeutic moiety, detection moiety or targeting moiety is not readily possible.

Furthermore, it is relatively difficult and hazardous to prepare PEG as explosive and highly toxic condensed ethylene oxide monomers are required. In addition, PEG has a limited storeability, i.e. an antioxidant is required for storage in order to avoid peroxide formation.

GB 1 164 582 describes a polyalkylenimine/polycarbonamide graft copolymer having as the backbone a linear polyimine wherein the imino nitrogen atoms are separated on the average by no more than 5 carbon chain atoms, having pendant from some or all of such nitrogen atoms polycarbonamide side chains having as repeating unit a carbonamido divalent radical with a chain of 3 to 18 carbon atoms between the amido nitrogen atom and the carbonyl group, said side chains having a number average molecular weight of at least 500.

WO 2009/112402 describes a heterofunctional polyoxazoline derivative of the general structure: $R_1$—{[N(COX)$CH_2CH_2]_o$-[N(COR$_2$)CH$_2$—CH$_2$)]$_n$-[N(COY)CH$_2$—CH$_2$)]$_m$}$_a$—Z wherein:

$R_2$ is independently selected for each repeating unit from an unsubstituted or substituted alkyl, an unsubstituted or substituted alkenyl, an unsubstituted or substituted aralkyl or an unsubstituted or substituted heterocyclylalkyl group;

X is a pendent moiety containing a first functional group;

Y is a pendent moiety containing a second functional group;

and m are each an integer independently selected from 1-50;

n is an integer selected from 0-1000.

WO 2009/112402 describes a random copolymer of linear polyethylenimine comprising two monomeric units, including a monomeric unit comprising a pendant moiety having the following formula: —CH$_2$CHR$^1$CONHCHR$^a$R$^b$;

wherein:

$R^1$ represents a hydrogen atom or a $C_1$-$C_6$ alkyl group, $R^a$ represents CH$_2$-imidazole;

$R^b$ represents COOR$^2$;

$R^2$ represents a hydrogen atom, a C1-C6 alkyl, aryl or aralkyl group, in which the alkyl group is a C1-C6 alkyl, n is a number comprised between 1 and 99% of the total monomers and m is a number comprised between 1 and 99% of the total monomers.

The international patent application also describes target molecule-polyoxazoline conjugates comprising a target molecule wherein the target molecule is a therapeutic moiety, a diagnostic moiety or a targeting moiety.

JP 2005161698 describes a recording material that is formed by providing a recording layer including an acylhydrazide compound and a diazo compound. The Japanese application contains a formula A40 that represents a 2-substituted oxazoline, wherein the 2-substituent is represented by —CH$_2$—CONH—NHX, wherein X is a p-substituted benzyl group.

Zarka et al. (*Amphiphilic Polymer Supports for the Asymmetric Hydrogenation of Amino Acid Precursors in Water*, Chem. Eur. J. 2003, 9, 3228-3234) describe the synthesis of amphiphilic, water-soluble diblock copolymers based on 2-oxazoline derivatives with pendent (2S,4S)-4-diphenylphosphino-2-(diphenylphosphinomethyl) pyrrolidine units in the hydrophobic block. The synthetic strategy involves the preparation of a diblock copolymer precursor with ester functionalities in the side chain; which were converted into carboxylic acids in a polymer-analogous step and finally reacted with the PPMligand in the presence of dicyclohexylcabordiimide yielding an tertiary amide linkage in between the polymer and the ligand.

Cesana et al. (*First Poly(2-oxazoline)s with Pendant Amino Groups*, Macromol. Chem. Phys. 2006, 207, 183-192) describe the preparation of a poly(2-oxazoline) with pendant amino groups starting from 2-oxazoline monomer with a Boc protected amino function, 2-[N-Boc-5-aminopentyl]-2-oxazoline (Boc-AmOx). This monomer could be converted via living cationic ring-opening polymerization to homopolymer. After quantitative deprotection, poly(2-oxazoline)s with pendant amino functions were obtained. Copolymerization with different monomer ratios of Boc-AmOx and 2-ethyl-2-oxazoline (EtOx) was performed. A cross-linking reaction with a bifunctional isothiocyanate (Ph(NCS)2) resulted in poly(2-oxazoline) hydrogels.

Luxenhofer (Thesis: *Novel Functional Poly(2-oxazoline)s as Potential Carriers for Biomedical Applications*, Technische Universität München (2007)) describes a poly(2-oxazoline) comprising 20 units of 2-methyl-2-oxazoline and 5 units of 2-aminoethyl-2-oxazoline. This polymer was cross-linked with hexamethylene diisocyanate to produce an amine hydrogel.

Liu et al. (*Shell Cross-Linked Micelle-Based Nanoreactors for the Substrate-Selective Hydrolytic Kinetic Resolution of Epoxides*, J. Am. Chem. Soc. 2011, 133, 14260-14263) describe amphiphilic poly(2-oxazoline) triblock copolymers. These copolymers are prepared from a monomer mixture that includes a cinnamate-functionalized oxazoline monomer that was prepared by a five step synthetic procedure yielding a 2-oxazoline monomer with a C$_{11}$ spacer in between the monomer ring and the cinnamate.

The polyoxazoline polymers with pendant amine containing units reported by Cesana et al. and Luxenhofer suffer from the disadvantage that the amine groups need to be protected. Furthermore, these protected amine-groups tend to interfere with the polymerization process, yielding rather poorly defined polymers. This latter disadvantage can be overcome by replacing the common initiators with a preformed oxazolinium triflate initiating moiety further complicating the polymerization process.

Conversion of the pendant amines in the aforementioned polyoxazoline polymers into an amide moiety yields functionalized polymers similar to those described by Liu et al. A disadvantage of these amide-containing polymers is that a primary amine is retained after hydrolysis, i.e. biodegradation, giving rise to toxic polymers.

In view of the problems mentioned above a need exists for polymers with excellent conjugating properties, causing less side effects and providing excellent delivery of small therapeutic molecules and biopharmaceuticals to the tissue involved. In addition, there is a need for a simple process for synthesizing these polymers in good yield and in a well-defined form.

SUMMARY OF THE INVENTION

The present invention relates to functionalized poly(2-oxazoline) polymers, which are very suitable as a carrier and/or delivery vehicle (conjugate) of drugs, such as small therapeutic molecules and bio-pharmaceuticals.

These polymers are characterized in that they comprise repeating units that are represented by the following formula

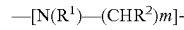

wherein
R$^1$ is R$^3$—(CHR$^4$)$_n$—CONH—R$^5$;
R$^2$ is selected from H and optionally substituted C$_{1-5}$ alkyl;
R$^3$ is CH$_2$, CO, C(O)O, C(O)NH or C(S)NH;
R$^4$ is selected from H and optionally substituted C$_{1-5}$ alkyl;
R$^5$ is H; an C$_{1-5}$ alkyl; aryl; or a moiety comprising a functional group that can be used for conjugation;
m is 2 or 3; and
n is 1-5; or n is 0 and R$^3$ is CH$_2$.

The polymers of the present invention provide a number of beneficial properties:

a large number of reactive moieties can be incorporated into the polymer via the side chains R$^1$;

a hydrophilic amide group is introduced in the side chain enhancing the solubility of the polymers compared to other side-chain functionalized polyoxazolines;

it is possible to orthogonally functionalize the chain ends as well as the side chains of the polymer, meaning that it is possible to formulate conjugates that simultaneously carry a drug, a targeting moiety and/or a label for imaging;

mechanical properties of the polymer can be controlled effectively by manipulating the level and the nature of the side chains R$^1$;

due to its hydrophilic/hydrophobic balance, the polymer can be soluble in organic fluids like ethanol and dichloromethane as well as in water;

the polymer has excellent amorphous properties with a glass transition temperature markedly higher compared to, for instance, polyethylene glycol;

the polymer has film forming capabilities and is easy to plasticize with limited amounts of plasticizers;

unlike PEG, the polymer may be co-polymerized, allowing the preparation of polymers with a wide range of properties;

the polymers in which R$^5$ is H or C$_{1-5}$ alkyl are highly water-soluble and can advantageously be used to improve the blood half life of conjugates;

the biodegradability of the secondary amide side chains allows release of side chain conjugated moieties.

The polymers of the present invention offer the important advantage that solubility, mechanical properties, biodegradability and loading of the polymer with active moieties can be manipulated within broad margins. Thus, the present polymer enables the preparation of a wide range of polymer carriers and polymer conjugates.

The invention further relates to conjugates of the aforementioned polymers with drugs, such as small therapeutic molecules and bio-pharmaceuticals. Also targeting moieties and diagnostic moieties may advantageously be conjugated with the presented polymer. The conjugates according to the present invention have amongst others a very good solubility, a tunable blood clearance profile and provide excellent protection against proteolytic degradation.

The present invention also relates to the use of the aforementioned conjugates in therapeutic treatment, prophylactic treatment or diagnosis. It particularly relates to the use in the treatment, prophylactic treatment or diagnosis of cancer.

Finally, the present invention also provides a method for preparing the polymers and conjugates described above.

DEFINITIONS

The term "amine" as used herein refers to a group comprising a nitrogen atom that is covalently bonded to at least one carbon, hydrogen or heteroatom.

The term "oxyamine" as used herein refers to a group comprising a nitrogen atom and an oxygen atom that are covalently bonded to each other as well as at least one carbon, hydrogen or heteroatom.

The term "thiol" as used herein refers to a group comprising a sulfur atom that is covalently bonded to at least one carbon or hydrogen atom.

The term "phosphine" as used herein refers to a group comprising a phosphor atom that is covalently bonded to at least on carbon, oxygen or hydrogen atom.

The term "alkyne" as used herein refers to a group comprising a carbon-carbon triple bond.

The term "alkene" as used herein refers to a group comprising with a carbon-carbon double bond.

The term "aryl" as used herein refers to aromatic groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, triazine, dichlorotriazine, tetrazine, pyridine, pyrazine, pyridazine, and pyrimidine.

The term "aldehyde" as used herein refers to groups with a terminal COH moiety.

The term "ketone" as used herein refers to groups with a CC(O)C moiety.

The term "acetal" as used herein refers to refers to groups with two single bonded oxygen atoms attached to the same carbon atom, such as, for example, a ketal group.

The term "ester" as used herein refers to groups with a CC(O)OC moiety.

The term "carboxylic acid" as used herein refers to groups with a CC(O)H moiety.

The term "carbonate" as used herein refers to groups with a COC(O) OC moiety.

The term "hydroxyl" as used herein refers to groups with an OH moiety.

The term "ether" as used herein refers to groups with a COC moiety.

The term "chloroformate" as used herein refers to groups with a COC(O)Cl moiety.

The term "azide" as used herein refers to groups with a NNN moiety.

The term "vinyl sulfone" as used herein refers to groups with a S(O2)C=C moiety.

The term "maleimide" as used herein refers to groups with a 2,5-pyrroledione moiety.

The term "isocyanate" as used herein refers to groups with a N=C=O moiety.

The term "isothiocyanate" as used herein refers to groups with a N=C=S moiety.

The term "epoxide" as used herein refers to groups with a three membered ring-structure comprising two carbon atoms and an oxygen atom, such as, for example, a glycidyl group.

The term "orthopyridyl sulfide" as used herein refers to groups with an S—S-2-pyridine moiety.

The term "sulfonate" as used herein refers to groups with a $S(O)_2O$ moiety.

The term "haloacetamide" as used herein refers to groups with a $NHC(O)CH_2X$ moiety with X=Cl, Br or I.

The term "haloacetic ester" as used herein refers to groups with a $OC(O)CH_2X$ moiety with X=Cl, Br or I.

The term "hydrazone" as used herein refers to groups with a C(O)N—N moiety.

The term "anhydride" as used herein refers to groups with a C(O)OC(O) moiety.

Whenever reference is made to a particular group, such as an alkyl group, unless indicated otherwise this group may be linear or branched.

The term "therapeutic moiety" as used herein refers to a compound having, attached to or separated from the polymer, pharmaceutically active properties.

The term "targeting moiety" as used herein refers to a moiety that, attached to or separated from the polymer, is able to bind to specific receptors or proteins in the body.

The term "diagnostic moiety" as used herein refers to compounds that, attached to or separated from the polymer, are able to be detected from outside the body.

The term "small molecule", "small therapeutic molecule" or small molecule drug" as used herein refers to a pharmaceutically active compound having a molecular weight, which is generally lower than 800 daltons and which compound is not a protein, peptide, oligonucleotide or fragment thereof.

The term "bio-pharmaceutical" as used herein refers to a pharmaceutically active compound having a molecular weight which is generally more than 800 daltons. However, these terms also encompass proteins, peptides, oligonucleotides and fragments thereof with a molecular weight lower than 800 daltons.

DETAILED DESCRIPTION OF THE INVENTION

A first aspect of the present invention relates to a polymer which comprises repeating units that are represented by the following formula (I)

—[N($R^1$)—(CH$R^2$)$m$]-   (formula I)

wherein $R^1$ is $R^3$—(CH$R^4$)$_n$—CONH—$R^5$;

$R^2$ is selected from H and optionally substituted $C_{1-5}$ alkyl;

$R^3$ is $CH_2$, CO, C(O)O, C(O)NH or C(S)NH;

$R^4$ is selected from H and optionally substituted $C_{1-5}$ alkyl;

$R^5$ is H; an $C_{1-5}$ alkyl; aryl; or a moiety comprising a functional group selected from an amine, an oxyamine, a thiol, a phosphine, an alkyne, an alkene, an aryl, an aldehyde, a ketone, an acetal, an ester, a carboxylic acid, a carbonate, a chloroformate, a hydroxyl, an ether, an azide, a vinyl sulfone, a maleimide, an isocyanate, an isothiocyanate, an epoxide, an orthopyridyl disulfide; a sulfonate; a haloacetamide; a haloacetic acid; a hydrazone; and an anhydride;

m is 2 or 3; and n is 1-5; or n is 0 and $R^3$ is $CH_2$.

In a preferred embodiment of the present invention $R^2$ is H or $C_{1-2}$ alkyl. Most preferably, $R^2$ is H.

In accordance with one embodiment of the invention $R^3$ is CO. Polymers in which $R^3$ is CO can suitably be produced by means of cationic polymerization of 2-oxazoline monomers. Alternatively, such polymers may suitably be produced from poloxazoline by removing the sidechains to produce a poly [2-alkyl-2-oxazoline/ethylene imine] followed by reaction with an activated ester, such as an acid chloride, or anhydride.

According to another embodiment, $R^3$ is $CH_2$. These polymers may suitably be produced from poloxazoline by removing the sidechains to produce a poly[2-alkyl-2-oxazoline/ethylene imine] followed by alkylation.

According to another embodiment, $R^3$ is C(O)O. These polymers may suitably be produced from poloxazoline by removing the sidechains to produce a poly[2-alkyl-2-oxazoline/ethylene imine] followed by reaction with an activated carbonate, such as chloroformate.

According to another embodiment, $R^3$ is C(O)NH. These polymers may suitably be produced from poloxazoline by removing the sidechains to produce a poly[2-alkyl-2-oxazoline/ethylene imine] followed by reaction with an isocyanate.

According to another embodiment, $R^3$ is C(S)NH. These polymers may suitably be produced from poloxazoline by removing the sidechains to produce a poly[2-alkyl-2-oxazoline/ethylene imine] followed by reaction with an isothiocyanate.

R4 is preferably selected from H and $C_{1-3}$ alkyl. Most preferably, $R^4$ is H.

In accordance with another preferred embodiment $R^5$ is a moiety comprising a functional group selected from amine, thiol, hydrazine, aldehyde, activated ester, maleimide or orthopyridyl disulfide. These functional groups are particularly preferred as they are able to bind covalently to a therapeutic moiety, both small molecules and bio-pharmaceuticals, but will be cleaved after having reached cancerous tissue due to the acidic tumor micro-environment, thereby releasing the therapeutic moiety.

It is particularly preferred to use an amine as the functional group. One of the major advantages of using an amine as functional group is that such tertiary amines are cationic when present in an aqueous solution, which enables them to interact with RNA and DNA of for example tumor cells. If an amine is used as a functional group it is particularly advantageous when $R_3$ is $CH_2$.

In a preferred embodiment of such a polymer, $R^5$ represents $R^6NR^{7'}R^{7''}$, wherein $R^6$ represents a covalent bond or an optionally substituted $C_{1-5}$ alkylene; and $R^{7'}$ and $R^{7''}$ are independently selected from H and $C_{1-5}$ In accordance with a particularly preferred embodiment $R^6$ is selected from a covalent bond, methylene, ethylene and propylene for reasons that these polymers display the highest solubility in water.

In accordance with another preferred embodiment $R^5$ is H or alkyl. Even more preferably, $R^5$ is H or methyl, most preferably $R^5$ is methyl.

In a further preferred embodiment of the present invention the integer m in formula (I) is 2.

The integer n preferably is 1-5, even more preferably 1-4 and most preferably 1-2.

The polymer according to the present invention typically has a molecular weight of at least 1,000 g/mol. Even more preferably, the polymer has a molecular weight in the range of 2,000-100,000 g/mol, most preferably of 5,000-50,000 g/mol.

In case $R^5$ is a moiety comprising a functional group as specified herein, the repeating units represented by formula (I) typically represents at least 2 mol %, more preferably 5-70 mol. % and most preferably 10-30 mol. % of the polymer.

In case $R^5$ is H or $C_{1-5}$ alkyl the repeating units represented by formula (I) typically represents at least 10-100 mol %, more preferably 20-100 mol. % and most preferably 40-100 mol. % of the polymer.

Besides the (monomeric) repeating units represented by formula (I), the present polymer may suitably contain other repeating units, notably other cyclic imino ether units, such as 2-oxazolines and 2-oxazines. In a particularly preferred embodiment of the present invention the polymer contains 0-98 mol. %, more preferably 30-95 mol. % and most preferably 70-90 mol % of repeating units represented by the formula (Y)

$$—[N(R^a)—(CHR^2)_m]—$$ (formula Y)

wherein $R^a$ represents C(O)H, C(O)$R^k$ or $R^k$, and wherein $R^k$ represents optionally substituted $C_{1-22}$ alkyl, optionally substituted cycloalkyl, optionally substituted aralkyl or optionally substituted aryl, and wherein the integer m is 2 or 3.

Preferably, $R^k$, represents an optionally substituted $C_{1-22}$ alkyl, more preferably $C_{1-10}$ alkyl and most preferably $C_{1-5}$ alkyl.

Repeating units represented by formula (I) and repeating units represented by formula (Y) together typically represent at least 50 wt. % of the present polymer. Even more preferably said repeating units together represent at least 80 wt. % and most preferably 100 wt. % of the repeating units contained in the present polymer.

The polymer according to the present invention may be a homopolymer or a copolymer. Most preferably, the present polymer is a poly-oxazoline copolymer.

It is further preferred that the polymer according to the present invention is a linear polymer.

A second aspect of the present invention relates to a conjugate of a polymer as described above, and at least one active moiety selected from a therapeutic moiety, a targeting moiety and a diagnostic moiety.

Preferably, the conjugate is obtained by allowing the active moiety, such as a therapeutic moiety, targeting moiety and/or diagnostic moiety to react with at least one of the functional groups in $R^5$ of the polymer. Advantageously, the active moiety is covalently bonded to the polymer.

Alternatively, the conjugate is a non-covalent assembly based on multiple non-covalent interactions such as hydrogen bonding or electrostatic interactions (e.g. involving tertiary amines within the polymer) with either complementary hydrogen bonding or oppositely charged macromolecules, including synthetic polymers, biopolymers and biopharmaceutics. In a preferred embodiment, conjugate is a layer-by-layer assembly of the polymer and a macromolecule. In another preferred embodiment, the conjugate is an assembly in the form of a non-viral vector for gene delivery.

The therapeutic moiety that is contained in the present conjugate preferably is able to inhibit a signal transduction cascade in a cellular system, interferes with the cytoskeleton or intercalates in the DNA double helix. It is further preferred that the therapeutic moiety, attached to or separated from the polymer, has anti-fibrotic, anti-angiogenic, anti-tumor, immune-stimulating or apoptosis-inducing activity. Particularly preferred therapeutic moieties are doxorubicin, daunorubicin, epirubicin, paclitaxel, mesochlorin, 5-fluorouracil and cis-platin.

The targeting moiety that is contained in the conjugate preferably comprises a folate group, since it is known that folate has a natural high affinity for the folate receptor protein, which is commonly expressed on the surface of many human cancers. Another preferred targeting moiety is the arginine-glycine-aspartate (RGD) sequence, as it targets integrin that is also overexpressed in cancerous tissues. The targeting moieties according to the present invention may also comprise antibodies, fragment-antigen-binding fragments (FABs), single domain antibodies (nanobodies), peptides or oligonucleotides, such as RNA, DNA and siRNA.

The diagnostic moiety is preferably selected from radiolabels (radionuclides), PET-imageable agents, SPECT-imageable agents, MRI-imagable agents and fluorescent probes.

A third aspect of the present invention relates to the above mentioned conjugate for use in the therapeutic treatment, prophylactic treatment or diagnosis of diseases or disorders, particularly cancer.

In accordance with a particularly preferred embodiment of said use, the conjugate is administered intravenously, subcutaneously or orally. Most preferably, the conjugate is administered subcutaneously or orally.

A fourth aspect of the present invention relates to a method of preparing a polymer as described above, wherein the method comprises:

providing a polymer comprising repeating units that are represented by the following formula (II)

  (formula II)

wherein:

$R^1$ is $R^3$—$(CHR^4)_n$—$COOR^8$;

$R^2$, $R^3$, $R^4$, m and n have the same meaning as described herein before;

$R^8$ is selected from optionally substituted $C_{1-22}$ alkyl, optionally substituted cycloalkyl, optionally substituted aralkyl, and optionally substituted aryl, reacting said polymer with an amine compound represented by the following formula (III)

  (formula III)

wherein:

$R^5$ has the same meaning as above.

In a preferred embodiment of the this method $R^8$ is a $C_{1-3}$ alkyl. Most preferably, $R^8$ is a methyl group.

In accordance with one embodiment of the present method $R^3$ is CO or C(O)O and the polymer comprising repeating units that are represented by formula (II), is obtained by:

hydrolysing a polymer comprising repeating units that are represented by the following formula (IV)

  (formula IV)

to produce a polymer comprising hydrolyzed repeating units that are represented by the following formula (V)

—[NH—$(CHR^2)$m]-  (formula V)

reacting the polymer comprising hydrolyzed repeating units with an ester represented by the following formula (VIa)

  (formula VIa)

or the following formula (VIb)

  (formula VIb)

wherein X' is selected from Cl, Br, I, OH or $OR^9$ where $R^9$ is an activating moiety, such as N-hydroxysuccinimide, para-nitrophenyl or pentafluorophenyl.

According to another advantageous embodiment of the present method, $R^3$ is $CH_2$, C(O)NH or C(S)NH and the polymer comprising repeating units that are represented by formula (II) is obtained by:

hydrolysing a polymer comprising repeating units that are represented by the following formula (IV)

  (formula IV)

to produce a polymer comprising hydrolyzed repeating units that are represented by the following formula (V)

  (formula V)

reacting the polymer comprising hydrolyzed repeating units with an ester represented by the following formula (VIIa)

$CH_2$=$CR^4$—$COOR^8$  (formula VIIa)

or the following formula (VIIb)

$CHX''$—$(CHR^4)_n$—$COOR^8$  (formula VIIb)

wherein X" is selected from Cl, Br, I, or an activated alcohol, such as triflate, tosylate, mesylate and nosylate;

or the following formula (VIIc)

O=C=N—$(CHR^4)_n$—$COOR^8$  (formula VIIc)

or the following formula (VIId)

S=C=N—$(CHR^4)_n$—$COOR^8$  (formula VIId).

In accordance with yet another embodiment of the present method $R^3$ is CO, and the polymer comprising repeating units that are represented by formula (II) is obtained by:

ring-opening polymerization of 2-substituted 2-oxazoline or a 2-substituted dihyro-1,3-oxazine represented by the following formula (VIII)

$R^c$—$(CHR^4)_n$—$COOR^8$  (formula VIII)

wherein $R^c$ represents a 2-substituted oxazoline or a 2-substituted dihyro-1,3-oxazine.

According to yet a further embodiment of the invention $R^3$ is CO and the polymer comprising repeating units that are represented by formula (II) is obtained by:

ring-opening polymerization of 2-substituted oxazoline or a 2-substituted dihyro-1,3-oxazine represented by the following formula (IX)

$R^c$—$(CHR^4)_n$—$CONHR^{5'}$  (IX)

wherein $R^c$ represents a 2-oxazoline or a 2-dihyro-1,3-oxazine, and wherein $R^{5'}$ is a group $R^5$ as defined herein before, said group being protected by protecting groups; and removing the protecting groups from $R^{5'}$.

Another aspect of the invention relates to a 2-substituted oxazoline or a 2-substituted dihyro-1,3-oxazine, wherein the 2-subtituent is represented by the following formula (X)

—$(CHR^4)_n$—$CONHR^5$  (X);

wherein $R^4$, $R^5$ and n are defined as herein before.

According to a particularly preferred embodiment of the aforementioned 2-substituted oxazoline or 2-substituted dihydro-1,3-oxazine $R^5$ is H or an $C_{1-5}$ alkyl.

The invention is further illustrated by means of the following non-limiting examples.

EXAMPLES

Example 1

A polyoxazoline polymer according to the present invention was prepared by a method comprising the following steps.

Aquazol 50 (poly(2-ethyl-2-oxazoline) (PEtOx), Mw 50,000) was subjected to controlled acidic hydrolysis to yield a poly[2-ethyl-2-oxazoline/ethylene imine] copolymer. Twelve percent of the initial 2-ethyl-oxazoline units was hydrolyzed.

This poly[2-ethyl-2-oxazoline/ethylene imine] was functionalized in a two-step approach by first coupling of methyl succinyl chloride, followed by the reaction of the methyl ester with ethylenediamine (30 equivalents in the absence of solvent) to yield an amine-side chain activated poly[2-(ethyl/amino-ethyl-amido-ethyl)-2-oxazoline] copolymer.

Example 2

A polyoxazoline polymer according to the present invention was prepared by a method comprising the following steps.

Aquazol 50 (PEtOx, Mw 50,000) was subjected to controlled acidic hydrolysis to yield a poly[2-ethyl-2-oxazoline/ethylene imine] copolymer. Ten percent of the initial 2-ethyl-oxazoline units was hydrolyzed.

This poly[2-ethyl-2-oxazoline/ethylene imine] was functionalized in a two-step approach by first coupling of methyl bromoacetate, followed by the reaction of the methyl ester with ethylenediamine (30 equivalents in the absence of solvent) to yield an amine-side chain activated poly[(2-ethyl-2-oxazoline)/(amino-ethyl-amido-methyl)] copolymer.

Example 3

A polyoxazoline polymer according to the present invention was prepared by a method comprising the following steps.

Aquazol 50 (PEtOx, Mw 50,000) was subjected to controlled acidic hydrolysis to yield a poly[2-ethyl-2-oxazoline/ethylene imine] copolymer. Ten percent of the initial 2-ethyl-oxazoline units was hydrolyzed.

This poly[2-ethyl-2-oxazoline/ethylene imine] was functionalized in a two-step approach by first coupling of methyl acrylate, followed by the reaction of the methyl ester with ethylenediamine (30 equivalents in the absence of solvent) to yield an amine-side chain activated poly[(2-ethyl-2-oxazoline)/(amino-ethyl-amido-ethyl)] copolymer.

Example 4

A polyoxazoline polymer according to the present invention was prepared by a method comprising the following steps.

2-(2-Methoxycarbonylethyl)-2-oxazoline was prepared following a literature procedure (A. Levy, M. Litt, J. Polym. Sci. A 1968, 6, 1883) followed by cationic ring-opening polymerization yielding the corresponding methylester functionalized homopolymer, poly(2-(2-methoxycarbonylethyl)-2-oxazoline).

Copolymerization of the 2-(2-methoxycarbonylethyl)-2-oxazoline monomer with 2-ethyl-2-oxazoline (50%) or 2-methyl-2-oxazoline (50%) yielded statistical copolymers.

These polymers were functionalized by the reaction of the methyl ester side chains with ethylenediamine (30 equivalents in the absence of solvent) to yield amine-side chain activated poly[amino-ethyl-amido-ethyl] copolymers.

Example 5

The poly(2-(2-methoxycarbonylethyl)-2-oxazoline) homopolymer from Example 4 was reacted with N-boc amino ethane amine by dissolving 0.8 g polymer in 2.5 mL N-boc amino ethane amine followed by 23 hours stirring at 80° C. $^1$H NMR spectroscopy in $CDC_3$ revealed that ~90% of the methyl ester units were converted into Boc-aminoethyl amido side chains. This polymer was further reacted with hydrochloric acid (HCl) by dissolving 850 mg of polymer in dichloromethane (30 mL), which was added dropwise to a HCl solution in ethyl acetate (0.175 mL, 2.98 mmol). After complete addition, the solution was stirred for 6 hours at room temperature. $^1$H NMR demonstrated the successful formation of the hydrochloric acid salt of amino-ethyl amido side chain functionalized polymer by disappearance of the Boc signal at 1.4 ppm.

Example 6

A polyoxazoline polymer according to the present invention was prepared by a method comprising the following steps.

Poly(2-ethyl-2-oxazoline) (PEtOx, Mw 10,000, degree of polymerization 100), prepared by living cationic ring-opening polymerization under microwave irradiation (140° C., 4 M monomer concentration in acetonitrile, methyl tosylate as initiator), was subjected to controlled acidic hydrolysis to yield a poly[2-ethyl-2-oxazoline/ethylene imine] copolymer. Eighteen percent of the initial 2-ethyl-oxazoline units was hydrolyzed.

This poly[2-ethyl-2-oxazoline/ethylene imine] was functionalized in a two-step approach by first coupling of methyl succinyl chloride yielding the methyl ester side-chain functionalized copolymer. Infrared (IR) spectroscopy clearly revealed the appearance of the characteristic methyl ester band at 1732 cm$^{-1}$ while proton nuclear magnetic resonance ($^1$H NMR) spectroscopy clearly showed the methyl ester signal at 3.7 ppm.

This polymer was further modified by reaction with various amines (at least 10 fold excess) in bulk, except hydrazine that was added as hydrazine mono-hydrate, at 70° C. in a closed reaction vessel. Successful coupling of the amine and the formation of the side chain amide substituents was demonstrated by the disappearance of the peak of the methyl ester at 3.7 ppm in the $^1$H-NMR spectra. Furthermore, new signals were detected for the incorporated amide side chains between 7 and 9 ppm when the measurements were conducted in DMSO-d6. Furthermore, the resulting polymers revealed a higher molar mass by size exclusion chromatography compared to the starting polymer that had a weight average molar mass ($M_w$) of $1.78*10^4$, a number average molar mass ($M_n$) of $1.67*10^4$ and a dispersity (Đ) of 1.1. Finally, IR spectroscopy revealed the disappearance of the band at 1732 cm$^{-1}$ while a secondary amide band (N—H bending vibration) appeared at 1570-1515 cm$^{-1}$. An overview of these reactions is provided in Table 1.

TABLE 1

| Amine | $^1$H-NMR (ppm) [1] | $M_w$ (×10$^4$) [2] | $M_n$ (×10$^4$) [2] | Đ [2] |
|---|---|---|---|---|
| Methylamine | 5.9 | 1.95 | 1.77 | 1.1 |
| Ethylamine | 7.8 | 1.95 | 1.77 | 1.1 |
| Propylamine | 7.9 | 1.95 | 1.78 | 1.1 |
| Dimethylamine | 6.3 | 1.95 | 1.78 | 1.1 |
| Hydrazine-monohydrate | 9 | 1.95 | 1.77 | 1.1 |
| Leucine | n.d. [3] | 2.03 | 1.8 | 1.1 |
| Glycine | n.d. [3] | 2.10 | 1.8 | 1.1 |
| Aminoethanol | n.d. [3] | 2.38 | 2.2 | 1.1 |
| Allylamine | 8.4 | 1.8 | 1.65 | 1.1 |

TABLE 1-continued

| Amine | $^1$H-NMR (ppm) [1] | $M_w$ (×10$^4$) [2] | $M_n$ (×10$^4$) [2] | Đ [2] |
|---|---|---|---|---|
| 1-amino-3-butyne | 8.4 | 1.79 | 1.67 | 1.1 |
| N,N'-dimethylethylene diamine | 8.2 | 1.81 | 1.66 | 1.1 |

[1] Chemical shift of the resulting amide proton in DMSO-d6
[2] Determined by means of size exclusion chromatography calculated against PMMA standards
[3] Measurements performed in methanol-d4 or CDCl₃ did not show this amide signal.

Example 7

A polyoxazoline polymer according to the present invention was prepared by a method comprising the following steps.

Poly(2-ethyl-2-oxazoline) (PEtOx, Mw 10,000, degree of polymerization 100), prepared by living cationic ring-opening polymerization under microwave irradiation (140° C., 4 M monomer concentration in acetonitrile, methyl tosylate as initiator), was subjected to controlled acidic hydrolysis to yield a poly[2-ethyl-2-oxazoline/ethylene imine] copolymer. Eighteen percent of the initial 2-ethyl-oxazoline units was hydrolyzed.

This poly[2-ethyl-2-oxazoline/ethylene imine] was functionalized in a two-step approach by first coupling of methyl-3-isocyanatopropionate (3 eq; reaction performed in dry chloroform for 5 minutes at 150° C. in a microwave oven) yielding the methyl ester side-chain functionalized copolymer in which the side chain is attached to the main chain via a urea linkage. Infrared (IR) spectroscopy clearly revealed the appearance of the characteristic methyl ester band at 1732 cm$^{-1}$ while proton nuclear magnetic resonance ($^1$H NMR) spectroscopy clearly showed the methyl ester signal at 3.7 ppm. SEC revealed a $M_w$ of 1.98×10$^4$, $M_n$ of 1.83×10$^4$ and a Đ of 1.1.

This polymer can be further modified by reaction of the methyl ester with various amines as exemplified in Example 6. This was demonstrated by reaction of the polymer with ethylamine by dissolving 0.3 g polymer in 2 mL ethylamine and heating overnight at 70° C. The success of the reaction was demonstrated by $^1$H NMR spectroscopy in DMSO-d6 revealing the specific amide signal at 7.9 ppm. IR spectroscopy also confirmed the reaction by disappearance of the band at 1732 cm$^{-1}$. SEC also confirmed an increase of molar mass after the reaction to a $M_w$ of 2.14×10$^4$, $M_n$ of 1.98×10$^4$ and a Đ of 1.1.

Example 8

A polyoxazoline polymer according to the present invention was prepared by a method comprising the following steps.

Poly(2-ethyl-2-oxazoline) (PEtOx, Mw 10,000, degree of polymerization 100), prepared by living cationic ring-opening polymerization under microwave irradiation (140° C., 4 M monomer concentration in acetonitrile, methyl tosylate as initiator), was subjected to controlled acidic hydrolysis to yield a poly[2-ethyl-2-oxazoline/ethylene imine] copolymer. Eighteen percent of the initial 2-ethyl-oxazoline units was hydrolyzed.

This poly[2-ethyl-2-oxazoline/ethylene imine] was functionalized in a two-step approach by first coupling of methyl-3-isothiocyanatopropanoate (3 eq; reaction performed in dry chloroform for 5 minutes at 150° C. in a microwave oven) yielding the methyl ester side-chain functionalized copolymer in which the side chain is attached to the main chain via a urea linkage. Infrared (IR) spectroscopy clearly revealed the appearance of the characteristic methyl ester band at 1732 cm$^{-1}$ while proton nuclear magnetic resonance ($^1$H NMR) spectroscopy clearly showed the methyl ester signal at 3.7 ppm. SEC revealed a $M_w$ of 2.28×10$^4$, $M_n$ of 2.05×10$^4$ and a Đ of 1.1.

This polymer can be further modified by reaction of the methyl ester with various amines as exemplified in Example 6. This was demonstrated by reaction of the polymer with ethylamine by dissolving 0.3 g polymer in 2 mL ethylamine and heating overnight at 70° C.

The success of the reaction was demonstrated by $^1$H NMR spectroscopy in DMSO-d6 revealing the specific amide signal at 8.1 ppm. IR spectroscopy also confirmed the reaction by disappearance of the band at 1732 cm$^{-1}$. SEC also confirmed an increase of molar mass after the reaction to a $M_w$ of 2.26×10$^4$, $M_n$ of 2.08×10$^4$ and a Đ of 1.1.

Example 9

The poly(2-(2-methoxycarbonylethyl)-2-oxazoline) homopolymer prepared in example 4 is reacted with hydrazine to yield the poly(hydrazone ethyl-2-oxazoline) homopolymer.

Example 10

The polymer of Example 1, poly[2-(ethyl/amino-ethyl-amido-ethyl)-2-oxazoline] copolymer, is reacted with doxorubicin by mixing both in an organic solvent, such that a conjugate of the polymer and doxorubicin is formed via an imine linkage (herein after: PDX-DOX-conjugate), which linker is acid-cleavable. Such an acid cleavable linker allows a rapid partial cleavage of the doxorubicin from the polymer already after transfer of the conjugate to the interstitial space of the tumor, i.e. extracellularly in close proximity to the target tumor cells, because tumor tissue is generally more acidic than non-tumor tissue. Thus, after save delivery of the conjugated drug to the tumor, the drug is liberated in or close to the tumor to carry out its action in the tumor tissue.

Example 11

The polymer from Example 9, poly(hydrazone ethyl-2-oxazoline) homopolymer, is reacted with DOX to yield the PDX-DOX conjugate in which the DOX is attached to the polymer via a pH cleavable hydrazone linkage.

Example 12

The copolymer consisting of ethyl and hydrazide side chains from Example 6, obtained by reaction of the methyl ester side chains with hydrazine, is reacted with DOX to yield the PDX-DOX conjugate in which the DOX is attached to the polymer via a pH cleavable hydrazone linkage.

Example 13

In order to direct the conjugated oxazoline polymers (PDX-DOX-conjugate) of Examples 11 and 12 to the cancerous tissue, the polymers are provided with targeting moieties. A very suitable targeting moiety is folate. Folate targeting is based on the natural high affinity of folate for the folate receptor protein (FR) which is commonly expressed on the surface of many human cancers. As such, folate-drug conjugates also bind tightly to the folate receptor and trigger cellular uptake of the conjugated polymer. Within the tumor tissue, the therapeutic moiety is released due to cleavage of the hydrazone linker.

The folate moiety is linked to the PDX-DOX-conjugates by coupling of the folate carboxylic acid group to the amine-terminus of the oxazoline polymer (DOX) that is introduced by endcapping of the polymers with potassium phtalimide followed by release of the amine by reaction with hydrazine.

Example 14

Besides folate the so called RGD-sequence is also very useful as targeting moiety since it actively targets integrins, which are overexpressed in cancerous tissue. Here the conjugated oxazolines (PDX-DOX conjugate) of Examples 11 and 12 are reacted with the cysteine moiety of CRGD using radical thiol-ene coupling to the alkene chain end functionality of the polyoxazoline that is introduced using propene tosylate as initiator.

Example 15

$^{18}$F labeling of amino-functionalized polyoxazoline is performed by reaction of the amine moieties with 4-nitrophenyl 2-[$^{18}$F]fluoropropionate, whereby the nitrophenyl activated ester is coupled to the amine.

The invention claimed is:

1. A conjugate of a polymer and at least one active moiety selected from a therapeutic moiety, a targeting moiety and a diagnostic moiety, the polymer comprising repeating units that are represented by the following formula (I):

  (I)

wherein:
$R^1$ is $R^3$—(CHR$^4$)$_n$—CONH—$R^5$;
$R^2$ is selected from H and optionally substituted $C_{1-5}$ alkyl;
$R^3$ is CO, C(O)O, C(O)NH or C(S)NH;
$R^4$ is selected from H and optionally substituted $C_{1-5}$ alkyl;
$R^5$ is H; an $C_{1-5}$ alkyl; aryl; or a moiety comprising a functional group selected from an amine, an oxyamine, a thiol, a phosphine, an alkyne, an alkene, an aryl, an aldehyde, a ketone, an acetal, an ester, a carboxylic acid, a carbonate, a chloroformate, a hydroxyl, an ether an azide, a vinyl sulfone, a maleimide, an isocyanate, isothiocyanate, an epoxide, orthopyridyl disulfide, sulfonate, halo acetamide, halo acetic acid, hydrazine, and anhydride;
m is 2 or 3; and
n is 1-5.

2. The conjugate according to 1, wherein $R^5$ is a moiety comprising an amine.

3. The conjugate according to claim 2, wherein $R^5$ represents $R^6NR^{7'}R^{7''}$, wherein:
$R^6$ represents a covalent bond or an optionally substituted $C_{1-5}$ alkylene; and
$R^{7'}$ and $R^{7''}$ are independently selected from H and $C_{1-5}$.

4. The conjugate according to claim 1, wherein the polymer has a molecular weight of 2,000-50,000 g/mol.

5. The conjugate according to claim 1, wherein the repeating units represented by formula (I) represent at least 5 mol. % of the polymer.

6. The conjugate according to claim 1, wherein the polymer contains 0-80 wt. % of repeating units represented by formula (X):

  (X)

wherein the repeating units represented by formula (X) are different from the repeating units represented by formula (I); and wherein $R^a$ represents C(O)H, C(O)R$^k$ or R$^k$; and R$^k$ represents optionally substituted $C_{1-22}$ alkyl, optionally substituted cycloalkyl, optionally substituted aralkyl or optionally substituted aryl.

7. The conjugate according to claim 1, wherein the conjugate is obtained by reacting the active moiety with at least one of the functional groups in $R^5$ of the polymer.

8. A method of therapeutic treatment, prophylactic treatment or diagnosis, the method comprising administering to a subject a conjugate according to claim 1.

9. A polymer comprising repeating units that are represented by the following formula (I):

  (I)

wherein:
$R^1$ is $R^3$—(CHR$^4$)$_n$—CONH—$R^5$;
$R^2$ is selected from H and optionally substituted $C_{1-5}$ alkyl;
$R^3$ is CO, C(O)O, C(O)NH or C(S)NH;
$R^4$ is selected from H and optionally substituted $C_{1-5}$ alkyl;
$R^5$ is H; an $C_{1-5}$ alkyl; aryl; or a moiety comprising a functional group selected from an amine, an oxyamine, a thiol, a phosphine, an alkyne, an alkene, an aryl, an aldehyde, a ketone, an acetal, an ester, a carboxylic acid, a carbonate, a chloroformate, a hydroxyl, an ether an azide, a vinyl sulfone, a maleimide, an isocyanate, isothiocyanate, an epoxide, orthopyridyl disulfide, sulfonate, halo acetamide, halo acetic acid, hydrazine, and anhydride;
m is 2 or 3; and
n is 1-2.

10. The polymer according to 9, wherein $R^5$ is a moiety comprising an amine.

11. The polymer according to claim 10, wherein $R^5$ represents $R^6NR^{7'}R^{7''}$, wherein:
$R^6$ represents a covalent bond or an optionally substituted $C_{1-5}$ alkylene; and
$R^{7'}$ and $R^{7''}$ are independently selected from H and $C_{1-5}$.

12. The polymer according to claim 9, having a molecular weight of 2,000-50,000 g/mol.

13. The polymer according to claim 9, wherein the repeating units represented by formula (I) represent at least 5 mol. % of the polymer.

14. The polymer according to claim 9, wherein the polymer further comprises repeating units represented by formula (Y):

  (Y)

wherein the repeating units represented by formula (Y) are different from the repeating units represented by formula (I);
wherein $R^a$ represents C(O)H, C(O)R$^k$ or R$^k$; and R$^k$ represents optionally substituted $C_{1-22}$ alkyl, optionally substituted cycloalkyl, optionally substituted aralkyl or optionally substituted aryl; and
wherein repeating units represented by formula (I) and repeating units represented by formula (Y) together represent at least 50 wt. % of the polymer.

15. A method of preparing a polymer according to claim 9, comprising reacting:
(a) a polymer comprising repeating units that are represented by the following formula (II):

  (II)

wherein:
$R^1$ is $R^3$—(CHR$^4$)$_n$—COOR$^8$;
$R^2$ is selected from H and optionally substituted $C_{1-5}$ alkyl;
$R^3$ is CO, C(O)O, C(O)NH or C(S)NH;

$R^4$ is selected from H and optionally substituted $C_{1-5}$ alkyl;
m is 2 or 3;
n is 1-2;
$R^8$ is selected from optionally substituted $C_{1-22}$ alkyl, optionally substituted cycloalkyl, optionally substituted aralkyl, and optionally substituted aryl; with (b) an amine compound represented by the following formula (III):

$$NH_2—R^5 \qquad (III)$$

wherein $R^5$ is H; an $C_{1-5}$ alkyl; aryl; or a moiety comprising a functional group selected from an amine, an oxyamine, a thiol, a phosphine, an alkyne, an alkene, an aryl, an aldehyde, a ketone, an acetal, an ester, a carboxylic acid, a carbonate, a chloroformate, a hydroxyl, an ether an azide, a vinyl sulfone, a maleimide, an isocyanate, isothiocyanate, an epoxide, orthopyridyl disulfide, sulfonate, halo acetamide, halo acetic acid, hydrazine, and anhydride.

16. The method according to claim 15, wherein $R^3$ is CO or C(O)O and wherein the polymer comprising repeating units that are represented by formula (II) is obtained by:

(a) hydrolysing a polymer comprising repeating units that are represented by the following formula (IV):

$$—[N(COR^b)—(CHR^2)_m]— \qquad (IV)$$

to produce a polymer comprising hydrolyzed repeating units that are represented by the following formula (V):

$$—[NH—(CHR^2)_m]— \qquad (V)$$

(b) reacting the polymer comprising hydrolyzed repeating units with an ester represented by the following formula (VIa):

$$C(O)X'—(CHR^4)_n—COOR^8 \qquad (VIa)$$

or the following formula (VIb):

$$C(O)X'—O—(CHR^4)_n—COOR^8 \qquad (VIb)$$

wherein X' is selected from Cl, Br, I, OH or $OR^9$ wherein $R^9$ is an activating group selected from N-hydroxysuccinimide, para-nitrophenyl and pentafluorophenyl.

17. The method according to claim 15, wherein $R^3$ is C(O)NH or C(S)NH and wherein the polymer comprising repeating units that are represented by formula (II) is obtained by:

(a) hydrolysing a polymer comprising repeating units that are represented by the following formula (IV):

$$—[N(COR^b)—(CHR^2)_m]— \qquad (IV)$$

to produce a polymer comprising hydrolyzed repeating units that are represented by the following formula (V):

$$—[NH—(CHR^2)_m]— \qquad (V)$$

(b) reacting the polymer comprising hydrolyzed repeating units with an ester represented by the following formula (VIIa)

$$CH_2=CR^4—COOR^8 \qquad (VIIa)$$

or the following formula (VIIb)

$$CHX''—(CHR^4)_n—COOR^8 \qquad (VIIb)$$

wherein X'' is selected from Cl, Br, I, or an activated alcohol; or the following formula (VIIc)

$$O=C=N—(CHR^4)_n—COOR^8 \qquad (VIIc)$$

or the following formula (VIId)

$$S=C=N—(CHR^4)_n—COOR^8 \qquad (VIId).$$

18. The method according to claim 17, wherein the activated alcohol is selected from the group consisting of triflate, tosylate, mesylate and nosylate.

19. The method according to claim 15, wherein $R^3$ is CO, and wherein the polymer comprising repeating units that are represented by formula (II) is obtained by:

(a) ring-opening polymerization of 2-substituted 2-oxazoline or 2-substituted dihydro-1,3-oxazine represented by the following formula (VIII):

$$R^c—(CHR^4)_n—COOR^8 \qquad (VIII)$$

wherein $R^c$ represents a 2-oxazoline or a 2-dihydro-1,3-oxazine.

20. A method of preparing a polymer according to claim 9, wherein $R^3$ is CO and wherein the polymer comprising repeating units that are represented by formula (II) is obtained by:

(a) ring-opening polymerization of 2-substituted oxazoline or a 2-substituted dihydro-1,3-oxazine represented by the following formula (IX):

$$R^c—(CHR^4)_n—CONHR^{5'} \qquad (IX)$$

wherein $R^c$ represents a 2-oxazoline or a 2-dihydro-1,3-oxazine, wherein R5' is protected by protecting groups; and (b) removing the protecting groups from $R^{5'}$.

* * * * *